(12) United States Patent  (10) Patent No.: US 9,652,996 B2
Chen et al.  (45) Date of Patent: May 16, 2017

(54) MEASURING COGNITIVE LOAD

(75) Inventors: Fang Chen, Eveleigh (AU); Kun Yu, Eveleigh (AU)

(73) Assignee: NATIONAL ICT AUSTRALIA LIMITED, Eveleigh, NSW (AU)

( * ) Notice: Subject to any disclaimer, the term of this patent is extended or adjusted under 35 U.S.C. 154(b) by 1120 days.

(21) Appl. No.: 13/371,656

(22) Filed: Feb. 13, 2012

(65) Prior Publication Data

US 2012/0282577 A1  Nov. 8, 2012

(30) Foreign Application Priority Data

May 4, 2011  (AU) ................................ 2011901661

(51) Int. Cl.
 *G09B 19/00* (2006.01)
 *G06K 9/00* (2006.01)
 *A61B 5/00* (2006.01)

(52) U.S. Cl.
 CPC ............ *G09B 19/00* (2013.01); *A61B 5/7267* (2013.01); *G06K 9/00416* (2013.01)

(58) Field of Classification Search
 CPC ......... A61B 5/164; A61B 5/165; A61B 5/167; G09B 19/00; G06K 9/00416
 USPC ........................................................ 434/155
 See application file for complete search history.

(56) References Cited

U.S. PATENT DOCUMENTS 5,562,104 A  10/1996  Hochberg et al.
6,546,134 B1  4/2003  Shrairman et al.
2004/0165774 A1*  8/2004  Koubaroulis ...... G06K 9/00409 382/179
2006/0072825 A1*  4/2006  Hullender et al. ............ 382/187
2007/0248267 A1*  10/2007  Bar-av .......................... 382/186
2008/0253659 A1*  10/2008  Walch ........................... 382/186
2009/0238461 A1*  9/2009  Koubaroulis ...... G06K 9/00409 382/186

(Continued)

FOREIGN PATENT DOCUMENTS

WO  2005/009223  2/2005
WO  2007/000030  1/2007

(Continued)

OTHER PUBLICATIONS

"Correction of Wild Points Within an Electronic Tablet," IBM Technical Disclosure Bulletin, NN87024042, vol. 29, Issue 9, Feb. 1, 1987.*

(Continued)

*Primary Examiner* — Michael Grant

(57) ABSTRACT

A computer implemented method for measuring a person's cognitive load comprises initially receiving 100 stroke data (FIG. 4, FIG. 5(a)) representative of hand-based strokes produced by a person 200 while performing a task. A processor 216 selects 104 a subset of the stroke data FIG. 5(c) that meets one or more predetermined stability criteria. A measure indicative of the person's cognitive load based on the subset of stroke data is determined 106. In this was the user's cognitive load in an objective, uniform and non-intrusive manner by analyzing the user's writing behavior. An analysis of all of a user's writing strokes will bias the evaluation result. The accuracy of the cognitive load measurement is increased by applying stability criteria to select the best strokes for further analysis. By disregarding unstable strokes the computation costs for determining the user's cognitive load is also improved.

16 Claims, 5 Drawing Sheets

(56) References Cited

U.S. PATENT DOCUMENTS

| | | |
|---|---|---|
| 2010/0152622 A1 | 6/2010 | Teulings |
| 2010/0217097 A1* | 8/2010 | Chen et al. .................. 600/301 |
| 2011/0217679 A1* | 9/2011 | Rosenblum .................. 434/155 |
| 2012/0082964 A1* | 4/2012 | Weitzman .................... 434/155 |
| 2012/0135386 A1* | 5/2012 | Zaneti .......................... 434/236 |

FOREIGN PATENT DOCUMENTS

| | | |
|---|---|---|
| WO | WO 2007000030 A1 * | 1/2007 |
| WO | 2009/149110 | 10/2009 |

OTHER PUBLICATIONS

Yu, Kun, et al, "Cognitive Load Evaluation of Handwriting Using Stroke-level Features," Proc. International Conference on Intelligent User Interfaces, (IUI' 11), Palo Alto, U.S.A. Feb. 2011, pp. 423-426.* http://www.nicta.com.au/people/chenf; downloaded on Sep. 12, 2013.*

Paas, F., Tuovinen, J. E., Tabbers, H. K., & Van Gerven, P. W. M. (2003). Cognitive load measurement as a means to advance cognitive load theory. *Educational Psychologist*, 38 (1), 63-71.

Yu, K., Epps, J. & Chen, F. (2011) Cognitive Load Evaluation with Pen Orientation and Pressure. *MMCogEms: Inferring Cognitive and Emotional States from Multimodal Measures*, Alicante, Spain.

Yu, K., Epps, J. & Chen, F. (2011) Cognitive load evaluation of handwriting using stroke-level features. *Proceedings of the 16th international conference on Intelligent user interfaces*. Palto Alto, United States of America.

Ruiz, N., Taib, R., Shi, Y., Choi, E. & Chen, F. (2007) Using pen input features as indices of cognitive load. *Proceedings of the 9th international conference on Multimodal interfaces*. Nagoya, Japan.

Van der Plaats, R. E & Van Galen, G. P. (1990) Effects of spatial and motor demands in handwriting. J. Mot. Behav., 22:361-385.

* cited by examiner

MEASURING COGNITIVE LOAD

RELATED APPLICATIONS

Incorporated herein by reference is the specifications of PCT applications No. PCT/AU2006/000914 (WO2010/037163) and PCT/AU2009/001289 (WO2010/037163). Also incorporated by reference is the specification of the Australia provisional patent application No. 2011901661 from which priority is claimed.

TECHNICAL FIELD

This invention concerns a method for measuring cognitive load. In other aspects the invention can be expressed as a computer system and as software that are used to perform the method.

The concept of cognitive load has been used in a variety of fields that deal with the human mind interacting with some external stimulants. The definition of cognitive load is slightly different in each field. For instance, in pedagogical literature cognitive load refers to the total amount of mental activity imposed on working memory at any instance in time; while in ergonomics literature it is described as the portion of operator information processing capacity, or resources that are required to meet cognitive task demands. Each field provides different methods to measure cognitive load.

In this specification the phrase "cognitive load" is defined as in the cognitive psychology literature, and its meaning is not a measurement of attention span, work load, stress, engagement or other external elements to a task. Cognitive load is defined here as the mental effort or demand required for a particular user to comprehend or learn some material, or complete some task [1]. Cognitive load is relative to both the user (i.e. their ability to process novel information) and the task being completed (i.e. complexity), at any single point in time. It is attributable to the limited capacity of a person's working memory and their ability to process novel information.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BACKGROUND ART

Conventional methods for measuring cognitive load, include:
subjective measures, such as self-rating scales;
physiological techniques, such as pupil dilatation, heart rate and galvanic skin responses;
task or performance based measures, such as critical error rates and task completion times; and
behavioural measures, such as speech disfluencies, self-talk etc.

There are a number of problems with these methods for measuring cognitive load, including:
some of the methods are intrusive and disrupt the normal flow of performing the task;
some of the methods are physically uncomfortable for the user;
cannot be conducted in real-time as they are too labour-intensive;
the data quality is potentially unreliable outside laboratory conditions; and
the data quality can be affected by outside factors, such as user's stress level.

Objectively quantifying cognitive load that can be applied uniformly across fields as a standard, or to allow comparison between subjects remains an open problem. In fact, historically, the most consistent results for cognitive load assessments have been achieved through self-rating subjective measures. These allow users to describe in fine detail their perceived level of cognitive load induced by various types of task.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

SUMMARY

In a first aspect there is provided a computer implemented method for measuring a person's cognitive load comprising:
(a) receiving stroke data representative of hand-based strokes produced by a person while performing a task;
(b) selecting a subset of the stroke data that meets one or more predetermined stability criteria; and
(c) determining a measure indicative of the person's cognitive load based on the subset of stroke data.

High cognitive load can affect a user's ability to perform a task. The aim here is to determine the user's cognitive load in an objective, uniform and non-intrusive manner.

The inventors have identified that the user's writing behaviours are reflective of the cognitive load of a user. The inventors have further identified that the writing behaviours are not uniformly reflective of a cognitive load experienced. That is an analysis of all of a user's writing strokes will bias the evaluation result. Accordingly, this aspect advantageously improves the accuracy of the cognitive load measurement by applying stability criteria to select the best strokes for further analysis. By disregarding unstable strokes the computation costs for determining the user's cognitive load is also improved.

The hand-based strokes may be made by a person's finger or with the aid of a pointing device such as a pen or stylus.

The hand based strokes may be made at an interface which receives the stroke data input.

The stroke data may be received by a device having a touch sensitive interface that the pointing device can contact. Alternatively, a device that is held by the person performing the hand-based movement, such as a pen with sensors incorporated that are able to sense the movement of the pen, such as a three-axis accelerometer and a pressure sensor. Alternatively a device that is able to track the hand movement itself, such as through the use of imaging techniques to capture finger movement. Even further, stroke data may be received in two or more of these ways.

The stroke data may be comprised of data points each having a time reference and a spatial reference. The spatial reference may be two dimensional or three dimensional. Each data point may further comprise a pressure value representing the pressure applied to an interface at each data point. Each data point may further comprise an altitude measure representing the tilt of the pen, stylus, finger or other pointing device used to produce the hand-based strokes. Each data point may further comprise an azimuth measure representing the rotation of the pen, stylus, finger or other pointing device used to produce the hand-based strokes.

The method may comprise identifying sets of data points that are representative of a stroke. A single stroke may be comprised of a set of data points that are adjacent in time series order and have a pressure value indicative of that the stroke is in contact with an interface, being a computer interface or otherwise.

The predetermined stability criteria may include one or more of:
  that points in the set of data points representing a stroke have stable velocity, that is the variation in the velocity is less than a threshold
  that points in the set of data points representing a stroke have stable pressure, that is the variation in the pressure is less than a threshold. To apply this criteria the method may further comprise determining the pressure of the stroke at each data point.
  that points in the set of data points representing a stroke have stable altitude, that is the variation in the altitude is less than a threshold
  that points in the set of data points representing a stroke have stable azimuth, that is the variation in the azimuth is less than a threshold
  the length of a set of data points representing a stroke is stable, that is the length is within a range of lengths, wherein the range of lengths is based on the lengths of multiple sets of data points representing strokes.

The one or more thresholds may be predetermined and constant. Alternatively, the threshold may be dynamic and/or dependent on the task and/or person.

Determining the measure may comprise identifying predetermined stroke features from the subset of stroke data, assigning each a value and combining the values to provide the measure. The stroke features may include one or more of:
  (i) pressure applied in the stroke, such as peak pressure, average pressure, pressure at the start of a stroke and pressure at the end of the stroke,
  (ii) stroke velocity, such as peak velocity, average velocity, velocity at the start of a stroke and velocity at the end of the stroke,
  (iii) length of the stroke,
  (iv) an altitude measure representing the tilt of the pen, stylus, finger or other pointing device used to produce the hand-based strokes,
  (v) an azimuth measure representing the rotation of the pen, stylus, finger or other pointing device used to produce the hand-based strokes,
  (vi) features (ii)-(v) for movement between strokes (inter-strokes).

The method may provide as output, such as displayed or stored in computer non-volatile memory.

In a further aspect, there is provided a computer system to measure a person's cognitive load while performing a task comprising:
  a receiver to receive stroke data representative of hand-based strokes produced by a person while performing a task, and
  a processor to select a subset of the stroke data that meets one or more predetermined stability criteria, and to determine a measure indicative of the person's cognitive load based on the subset of stroke data.

In yet a further aspect there is provided software that when executed by a computer, causes the computer to perform the method of measuring a person's cognitive load as described above.

Optional features of the first aspect are equally optional features of the other aspects of the invention described here.

BRIEF DESCRIPTION OF THE DRAWINGS

An example of the invention will now be described wherein:
FIG. 5 is an example of selecting a subset of stroke data that meets one or more predetermined stability criteria.

BEST MODES

In complex, data-intense situations, users can experience high levels of cognitive load. This can interfere with their ability to complete a task and also adversely affect their performance of the task.

The intelligent user interface system of this example, which is aware of the user's changes in cognitive load can alleviate this problem by implementing output strategies to modulate the pace, content, and format of the output interaction in real-time, such as to simplify the user's task. Alternatively, or in addition the output strategies may be based on determining the resources needed by the user to complete the task effectively and efficiently. The interface is aware of the user's cognitive load based on an assessment of the hand-based strokes of the user's written input.

Figure 1:
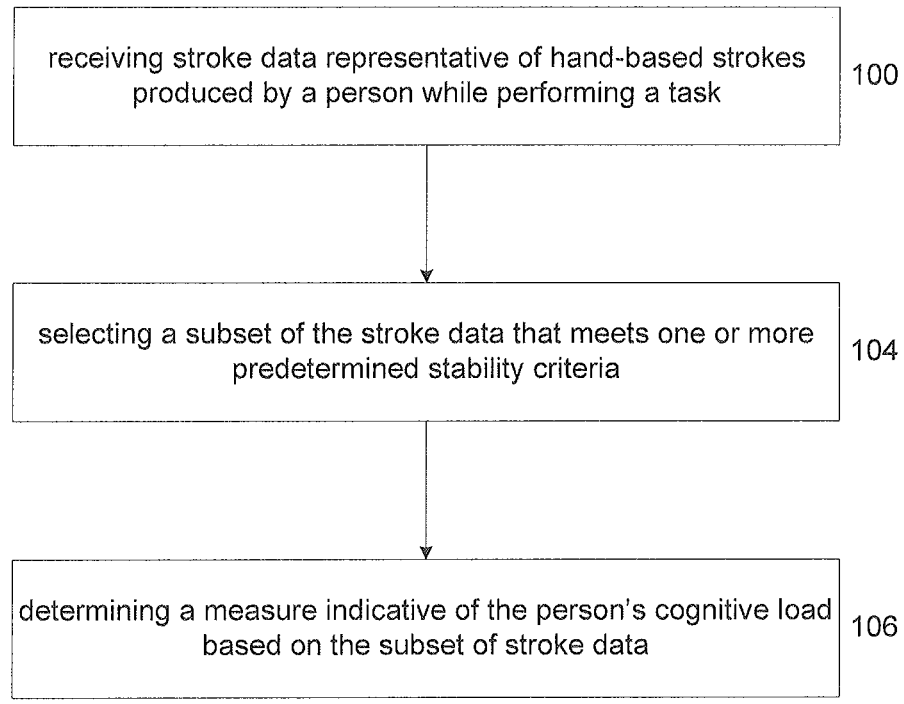
FIG. 1 is a flow chart of this example of the current invention.
Figure 2:
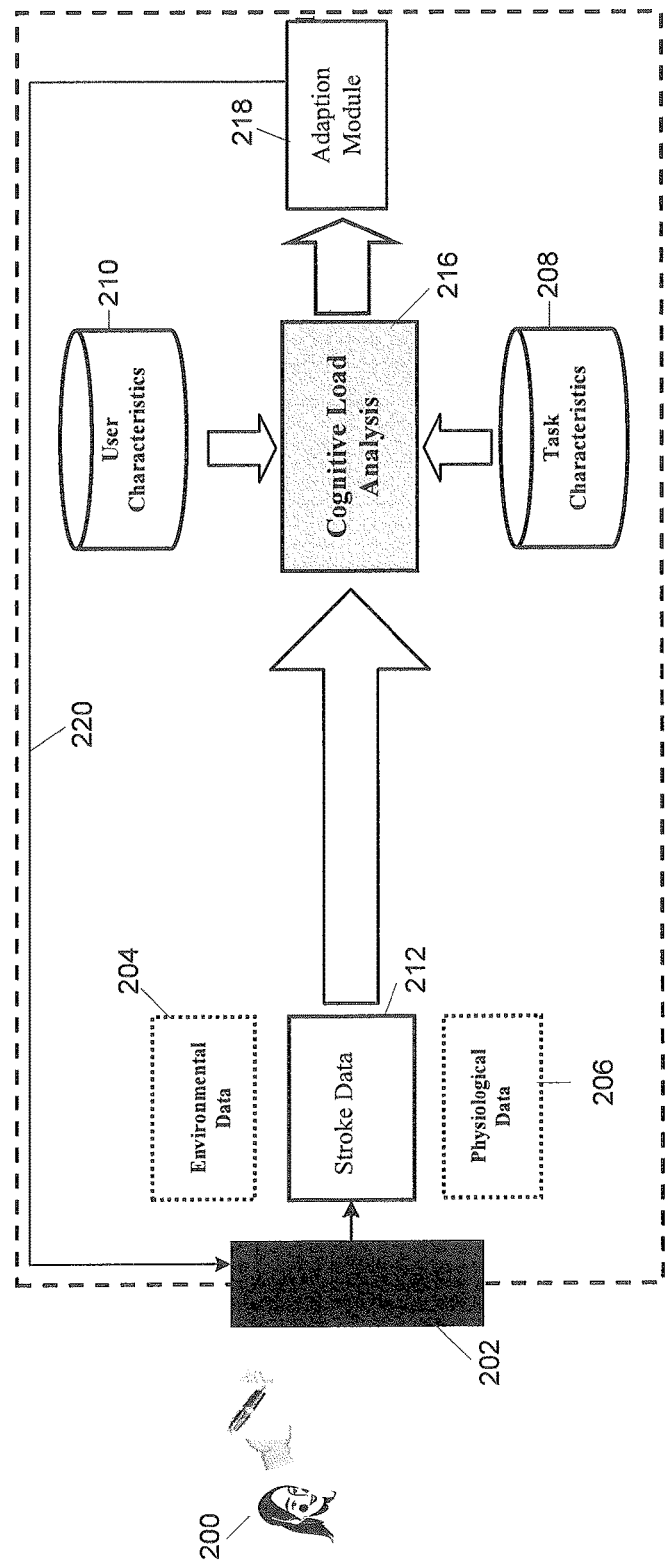
FIG. 2 is a high-level block diagram of the cognitive load measurement process.

The method of measuring the user's cognitive load from which these output strategies will be based will now be described with reference to FIGS. 1 and 2.

This example relates to on-line distance education. The learning cognitive load is a measure of the mental processing demand involved in learning tasks. When this demand is too high or low, learning is ineffective.

A written analysis-based learning difficulty diagnosis program, which measures learning cognitive load, would contribute immediately to the improvement of education for rural and dispersed learners. The determined cognitive load is provided in real time to the teacher or tutor to provide clearer information about students' learning difficulties than currently available diagnostic methods. The measurements of cognitive load can also be used to diagnose learning difficulties in conventional educational settings, and to assist in the development of instructional programs.

Implementations of this invention could help provide both teachers and students immediate feedback about their learning effectiveness.

In performing the learning task, the user 200 interacts with the computer system by providing stroke based input. In this example the computer system is a personal computer.

In performing the learning task, the user 200 interacts with the human-computer interface 202 of the computer. The user interacts by using either:
  a pointing device, such as a stylus or pen, or
  their hand, typically their index finger.

In this example a stylus is used. The interface 202 is a touch sensitive display that is able to display the graphical user interface and receive 100 stroke data input by use of the pointing device on the touch sensitive display.

In this example the interface can display a video conference screen of the teacher during a tutorial or questions that form a test and the hand-based strokes data are received from the person 200 writing sentences on an interface 202. In this case the touch sensitive display is a receiver. Alternatively, receivers would be other input devices to the personal computer, such as the stylus itself that can sense and provide the input data as described below.

The interface can also include further input devices (not shown) to receive word based input produced by a person while performing the task. For example, input devices such as a keyboard to type answers to the question and/or a microphone to record the speech of the user 200 as they perform the task, such as answering questions posed by the tutor on the video link or questions of the test.

Further inputs devices are provided such as devices to provide data on environmental factors 204, such as a thermometer, and devices to provide data on physiological factors 206, such as a heart rate monitor to provide heart rate data as input.

Task profiles/databases 208 stored in memory of the computer containing task characteristics, such as task type, task complexity or difficulty, current stage or state of the task, completion rate etc.

User profiles/databases 210 stored in the memory of the computer containing user characteristics such as gender, age, and education.

The computer also includes a processor 216 to cause the computer to perform the required interaction in accordance with instructions provided by software installed on the computer, that is in this example driving the interface 202 to perform the method described here.

Figure 3:
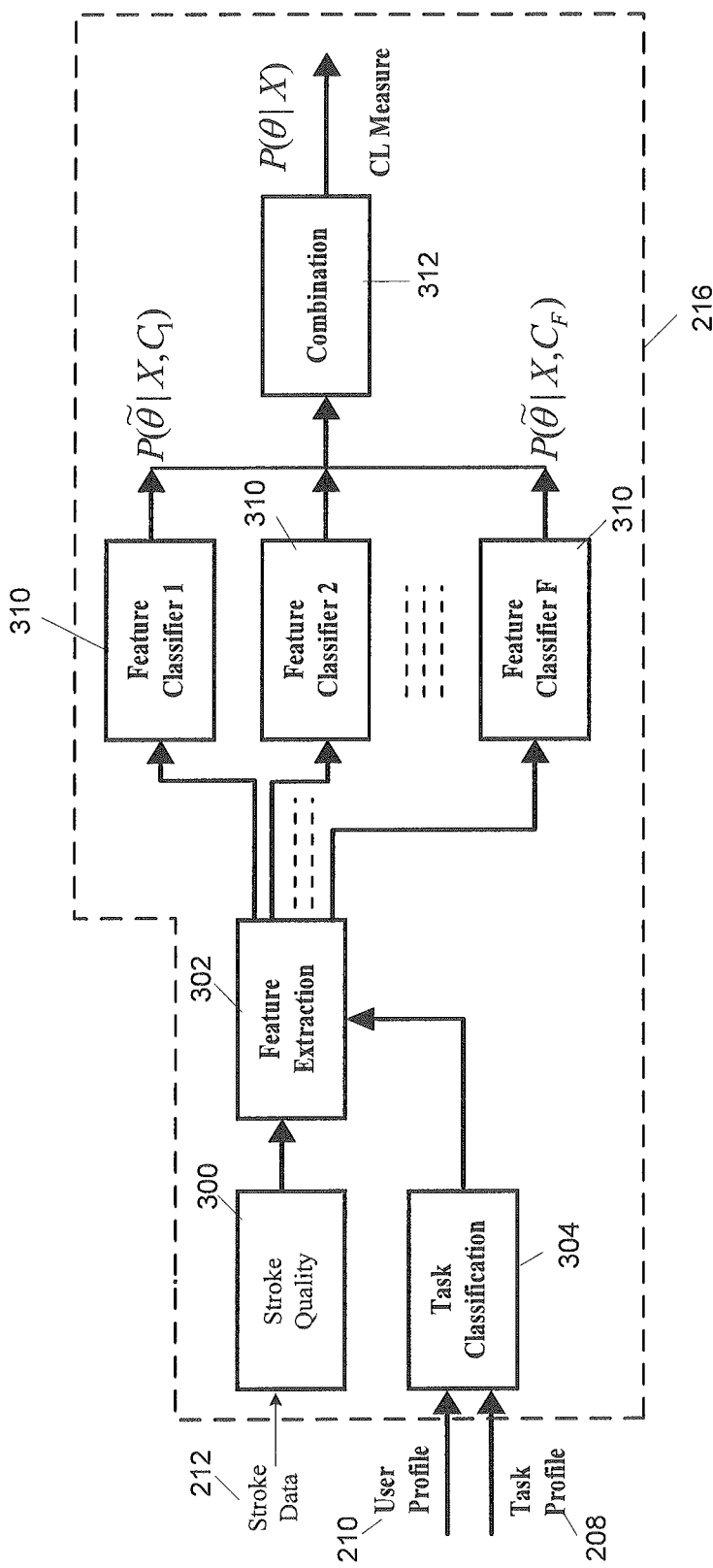
FIG. 3 is a schematic representation of this example of the current invention.

The processor is shown schematically in FIG. 3 as the cognitive load analysis module 216 that receives the input data 212, 204 and 206, and user characteristic data 210, and task characteristic data 208 to determine a cognitive load measure 218 of the user.

This measure is provided as input to adaptation module 218 that operates to adjust the interface 202 in real time. For example adaptive hints according to the current cognitive load including text input on pen interfaces with automatic word completion based on a lexicon or word translation based on a dictionary. Other examples include adjusting the difficulty of a pen game being played according to the detected cognitive load, or writing interface adaption based on the cognitive load measurements to improve the writing education efficiency.

System Framework

In this example, during training, the user 200 is required to complete a set of tasks using the interactive interface 202. These tasks rely mainly on the person 200 writing with the use of a stylus on the touch sensitive display 202. As they complete the tasks, their hand-based movements are received as stroke data 212 by the computer.

More specifically, the user 200 is assigned a set of tasks for the user to complete while interacting with the interface 202. These tasks must have definite variation in complexity so that the measurements at each cognitive load level can be taken separately. Different methods of feature classification will be derived but not all may be applied depending on the task application instance.

As the user 200 completes the tasks, their stroke data 212, environmental data 204 and physiological data is received and stored by the computer in real time.

The cognitive load analysis component 216 receives the stroke data (including time alignment information) and identifies any applicable set of selected feature categories for each level of cognitive load. The feature categories that are chosen depend on the classified task application area. Therefore, only a few task specific features will be extracted by the cognitive load analysis unit when in use.

Cognitive Load Evaluation

Referring now to FIG. 3 the method performed by the cognitive load analysis module 216 will now be described.

In control measurement mode (i.e. training), the module extracts 302 and records the relevant set of stroke features from the stroke data at each level of cognitive load along with the user profile 210 and task 208 characteristics. All available user and task attributes are divided into homogeneous clusters based on clustering algorithm, such as Decision Tree. Each cluster can then be assigned a task ID where corresponding stroke features can be tagged accordingly. Features from the higher cognitive load tasks can be assigned higher weights and given a larger significance during the actual measurement process later.

In actual measurement mode (i.e. real-time assessment of cognitive load) the task is classified in 304, where a fast search is done to retrieve the task ID, for example, for an online learning or examination task with its difficulty level, subject type etc., from the Decision Tree built during training. The module 304 can also cover other application/task categories such as call centre operator training, reading comprehension and collaborative problem solving.

Figure 4:
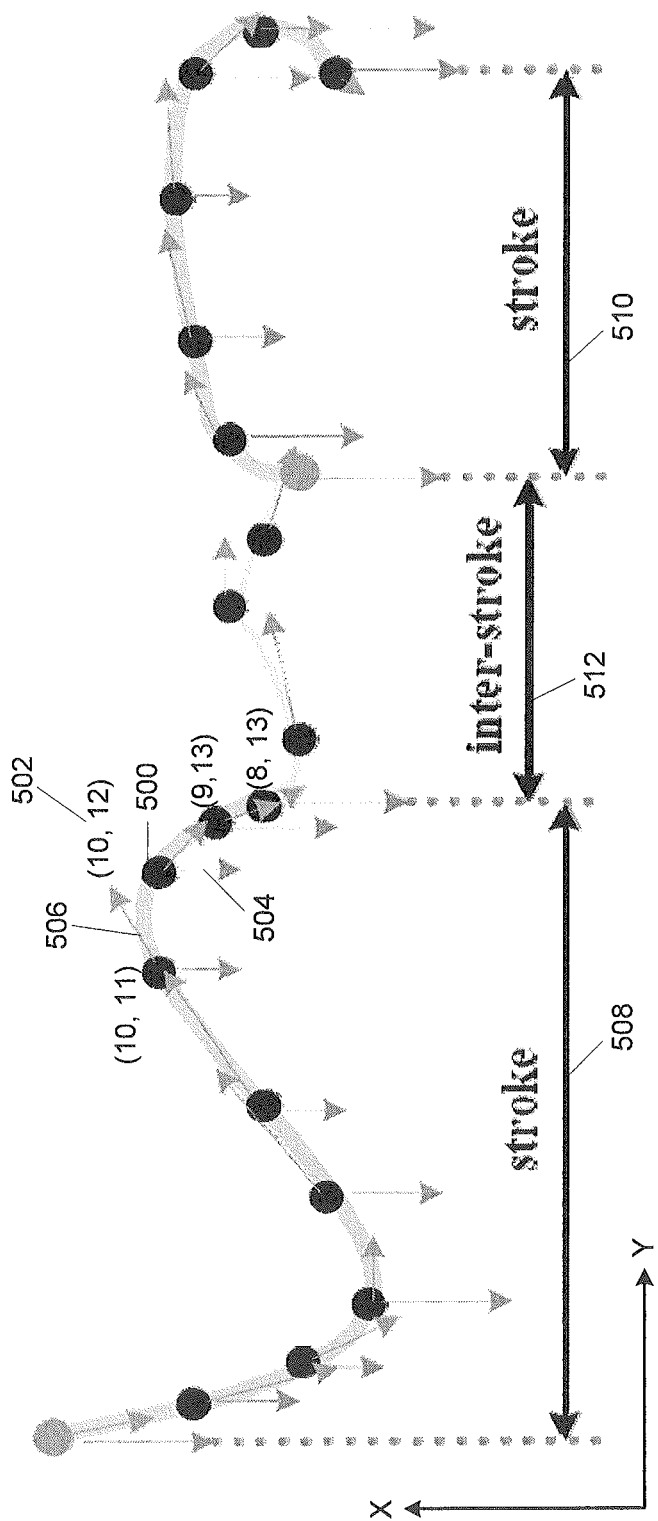
FIG. 4 is a schematic representation of stroke data.

The stroke quality evaluator 300 receives the stroke data to identify 104 the low-quality unstable strokes, that is selecting from the stroke data only a subset of the data that is representative of strokes that are higher in quality for use in cognitive load measurement. First individual strokes represented in the data are identified. In this example and referring to FIG. 4, the stroke data is a set of adjacent data points (one point identified at 500). Each data point provides:

a spatial reference, that is the location of the stylus tip on the graphical interface, such as an (x,y) coordinate 502. Location of the stylus tip could be detected with built-in electromagnetic induction sensors when it is not touching the interface, or with other imaging devices set along the writing interface.

the pressure applied by the stylus on that point, such as a integer proportional to the amount of pressure. The amount of pressure is shown by the length of the arrows 504 a timing reference.

The stroke quality evaluator 300 also determines the velocity at each point. The vector for velocity is shown in FIG. 5 as arrows (one shown at 506) where the magnitude is a determined speed at that data point and the direction of the arrow is the direction of motion at that data point.

In this example the time between the data points in the series are the same.

A stroke may be produced by the user in the process of writing words, drawing or otherwise navigating the graphical interface. A stroke is identified from the received stroke data by the cognitive load analysis module 216 as a set of adjacent data points in time series order, where all the points in set have a pressure measure indicative that stylus is at least in contact with the interface 202. In FIG. 5 two strokes 508 and 510 are identified.

"Interstrokes" are also identified where the stylus is not in contact with the touch sensitive display. An interstroke is comprised of adjacent data points in time series order that each have a status (pressure) measure indicative that the stylus is not in contact with the interface.

The stroke quality evaluator 300 assesses each stroke based on the following stability criteria:

Stable Velocity

The velocity at each data point of stroke is assessed for stability. That is a stroke is only considered stable if the variance in velocity of each point in the stroke is less than a predetermined threshold:

$$\text{var}(V) < T_V$$

where

V is the velocity of each data point of a stroke
$T_V$ is a predetermined threshold Stable Pressure The pressure at each data point of stroke is assessed for stability. That is a stroke is only considered stable if the variance in pressure for each point in the stroke is less than a predetermined threshold:

$$\text{var}(P) < T_P$$

where

P is the pressure of each data point of a stroke
$T_P$ is a predetermined threshold Stable Length The stroke is stable if its length is within a range that is dependent on the average length of the strokes within the stroke data. A stroke is considered stable where:

$$L(s_i) > \alpha \frac{1}{N} \sum_{i=1}^{N} L(s_i) \text{ and } L(s_i) < \beta \frac{1}{N} \sum_{i=1}^{N} L(s_i)$$

where $s_i$ is the data points of one stroke
N is the number of strokes
α and β are coefficients of the evaluation criteria Stable Azimuth The azimuth of the stylus at each data point of stroke is assessed for stability. This can also be viewed as the angle between the projection of the stylus on the touch sensitive display and the horizontal/vertical axis of the display during a stroke. A stroke is only considered stable if the variance in azimuth for each point in the stroke is less than a predetermined threshold:

$$\text{var}(Az) < T_{az}$$

where

Az is the azimuth of the stylus of each data point of a stroke
$T_{az}$ is a predetermined threshold Stable Altitude The altitude of the stylus at each data point of stroke is assessed for stability. This can also be viewed as the angle between the screen of the touch sensitive display and the stylus at each data point. A stroke is only considered stable if the variance in altitude for each point in the stroke is less than a predetermined threshold:

$$\text{var}(Al) < T_{al}$$

where

Al is the altitude of the stylus of each data point of a stroke
$T_{al}$ is a predetermined threshold It can be seen that stability is looking for limited window of change in the particular input being measured between datapoints. The thresholds are determined based on the analysis of individual writing history, and it is expected to be updated with personal writing accumulations.

Stability could be either user-specific or generic. User-specific stability is based on the historical records of the writing habits of the specific user, as an adaptive model that fits the user in most writing behaviours. Generic stability criteria may be focused on a universal model for a group of people in concern, and could be evaluated based on the common writing devices used, the writing circumstances, and the type of writing content, etc.

In this example, only strokes that satisfy at least three stability criteria are selected and provided to the feature extractor module 302 for further analysis. Benchmark calculation includes steps such as decision of the threshold for respective criterion, and thus to prioritize some stroke quality measurements instead of others.

Based on the task classification 304, the feature extractor module 302 identifies from the stable stroke data the stroke features that are predetermined as relevant to that classification of task. For example, when the task is classified as a text writing task, the predetermined structural features extracted from the stroke data can include stroke length and writing velocity. Weights are then assigned in 310 to enhance the selected features based on the classification.

Then the module 216 combines 312 the weighted features 310 to determine the measure 106 of cognitive load based on the stroke data input of the user 200. The combination mechanism is based on a probabilistic framework that combines various classifiers 310 together. This combination mechanism can be performed as described in the co pending patent application, published as WO2006AU00914. Various models can be used to build the feature classifiers. Some feasible ones include Gaussian mixture models, hidden Markov models, linear discriminate analysis, decision trees, and artificial neural networks. For example, classification scores for word-duration features can be combined with those scores for the word-category-frequency features, to improve the accuracy and robustness of the cognitive load measurement.

The result of the combination 312 is output and it represents the measure of cognitive load being experienced by a user 200 for a particular task. For example, the measure may be a scale between 1 to 10, where 10 represent high cognitive load. The measure will typically change over the course of the task.

Depending on the proximity of this measure to an optimized pre-set cognitive load target level for that task, the next task or system output or response is verified for appropriateness or changed by the adaptation module 218. For example, in the case of a distance education tutorial, if the cognitive load is too low, this feedback may be provided in real time to the tutor who can then accelerate the progress of the tutorial. If the cognitive load is too high, the interface can be automatically programmed to minimise all open applications displayed on 202 to the user (i.e. graphs on display) and to only show the video display of the tutor.

The measure may be displayed in real time, such as on a display back to the user or to a remote party monitoring the user, such as a teacher. The measures may be stored and used in further analysis. For example, statistical inferences could be made. For example, the task could be a test for employment. If the collected measures indicate that all candidates experienced high cognitive load from the beginning it could indicate that the difficulty of the task is set too high.

The measure may also be stored in permanent computer readable media for later retrieval, such as stored as a change in score in time series. The measure may also be communicated over a local or wide area network to a different computer.

A graphical representation of selecting a subset of strokes is show in FIG. 5.

Figures 5A, 5B, 5C:
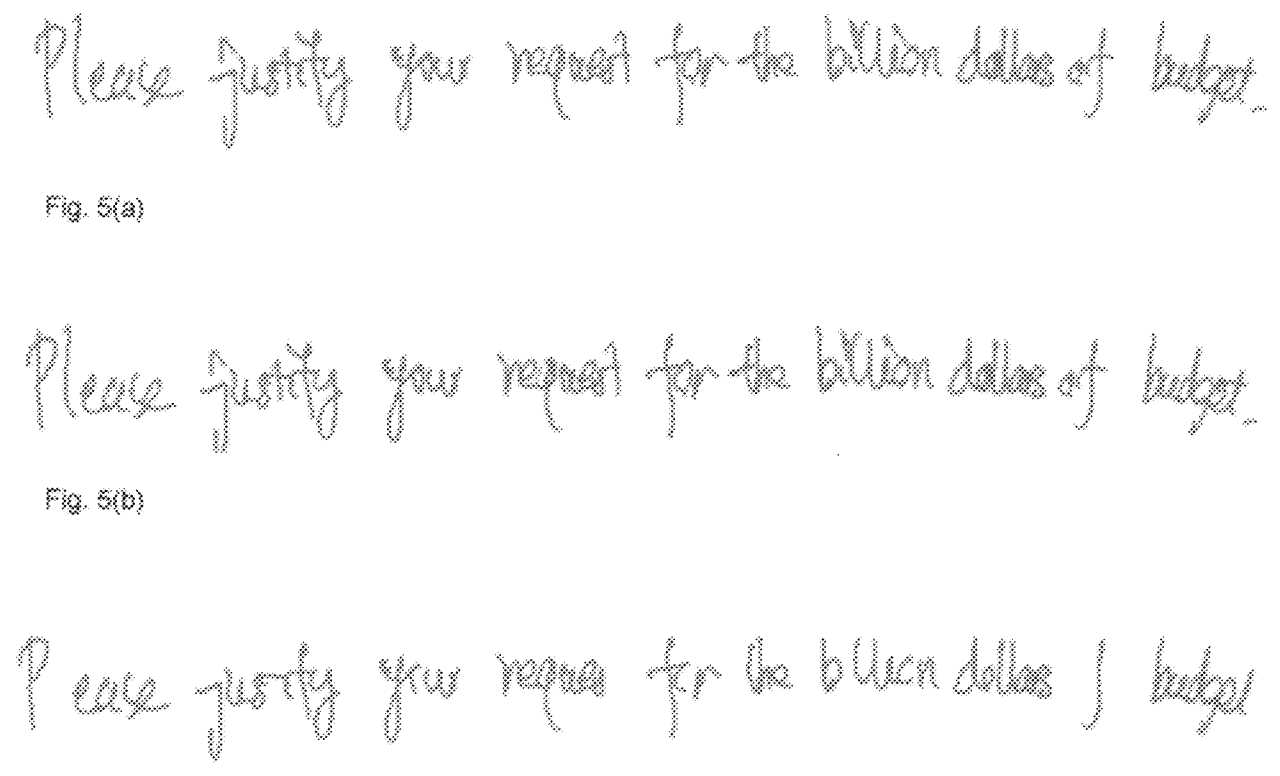

FIG. 5(a) shows the original stroke data, in this case a sentence written by a user at a computer interface using a stylus.

In this example the stability criteria was based on a combination of:
   stroke velocity, that is strokes that had a high velocity were considered unstable; and
   length of the stroke, that is strokes that had a short length were considered unstable.

The strokes that did not satisfy this stability criteria are shown at 500 in FIG. 5(b) in darker shade.

That leaves the remaining strokes as shown in FIG. 5(c), that is FIG. 5(c) represents the subject of stroke data that will be used to determine a measure indicative of the user's cognitive load.

This example has concentrated on the education environment however it could be used with many other applications such as in clinical environments where the health of the patient is being assessed. Alternatively it could be used as part of a recruitment screening or other cognitive profiling or workforce optimisation scenarios.

The interface 202 can be any device that supports interactions with a pen or touch interactions. In the case of finger interactions, azimuth and altitude measurements may relate to the user's finger.

The extracted features may depend on the device 200 that is used in performing the task, as different sensor technologies may be applicable on pen devices, resulting in different pen parameters and resolutions, e.g. capacitive interfaces are sensitive to contact (iphone), resistive interfaces could detect pressure, and electromagnetic screens have high resolution of movements.

For example, the interstrokes could also be evaluated for quality 300 and features extracted 302 and used to determine cognitive load.

In this example the processor has been local to the interface. In alternate embodiments the stroke data may be produced by the person remote from the processor, such as over a network.

It will be appreciated by persons skilled in the art that numerous variations and/or modifications may be made to the invention as shown in the specific embodiments without departing from the scope of the invention as broadly described.

For example, the method may not be performed on all data points that are received that define the stroke data, but rather a reduced set to assist in reducing complexity further and processing time.

It should be understood that the techniques of the present disclosure might be implemented using a variety of technologies. For example, the methods described herein may be implemented by a series of computer executable instructions residing on a suitable computer readable medium. That may be a personal computer, smart phone or tablet.

Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "selecting" or "processing" or "computing" or "calculating", "receiving" or "determining" or "displaying" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

REFERENCES

[1] F. Paas, et. al., "Cognitive load measurement as a means to advance cognitive load theory". *Educational Psychologist*, 2003, 38, 63-71.

The invention claimed is:

1. A computer implemented method for changing an output of a computer system based on a determination of a person's cognitive load, the method comprising:
   (a) receiving, at a processor of a computer system from an interactive interface of the computer system, stroke data sensed by the interactive interface, the stroke data comprising data points, each having a time reference and a spatial reference, wherein the stroke data is representative of hand-based strokes produced by a person while performing a task on the computer system via the interactive interface;
   (b) identifying, by the processor, sets of data points in the stroke data that have adjacent spatial references for each time reference in time series order, each of the sets of data points representing an individual hand-based stroke;
   (c) determining, by the processor, that one or more of the sets of data points in the stroke data meets one or more predetermined stability criteria by having a variance that is less than a threshold and selecting, by the processor, the one or more of the sets of data points;
   (d) identifying, by the processor, one or more predetermined stroke features in the selected one or more of the sets of data points and determining, by the processor, a measure indicative of the person's cognitive load based on the one or more predetermined stroke features identified in the selected one or more of the sets of data points; and
   (e) automatically changing an output of the computer system, via the processor, based on the measure indicative of the person's cognitive load to alleviate or increase the person's cognitive load.

2. The computer implemented method according to claim 1, wherein the hand-based strokes are made by a person's finger or with the aid of a pointing device.

3. The computer implemented method according to claim 1, wherein each data point further comprises a pressure value representing a pressure applied to an interface at each data point.

4. The computer implemented method according to claim 1, wherein each data point further comprises an altitude measure representing a tilt of a pen, stylus, finger or other pointing device used to produce the hand-based strokes.

5. The computer implemented method according to claim 1, wherein each data point further comprise an azimuth measure representing a rotation of a pen, stylus, finger or other pointing device used to produce the hand-based strokes.

6. The computer implemented method according to claim 3, wherein identifying, by the processor, sets of data points, each representing a hand-based stroke, includes identifying one or more sets of data points that have a pressure value indicative that the stroke is in contact with an interface.

7. The computer implemented method according to claim 1 or 6, wherein the predetermined stability criteria includes one or more of:
   that points in the one or more sets of data points representing a stroke have stable velocity,
   that points in the one or more sets of data points representing a stroke have stable pressure,
   that points in the one or more sets of data points representing a stroke have stable altitude,
   that points in the one or more sets of data points representing a stroke have stable azimuth,
   the length of a the one or more sets of data points representing a stroke is stable.

8. The computer implemented method according to claim 7, wherein stability is determined with reference to the threshold.

9. The computer implemented method according to claim 7, wherein the length of a set of data points is stable where the length is within a range of lengths that is based on the lengths of multiple sets of data points representing strokes.

10. The computer implemented method according to claim 8, wherein the threshold is dynamic and/or dependent on the task and/or person.

11. The computer implemented method of claim 1, wherein determining the measure comprises assigning a value to each predetermined stroke feature identified from the one or more sets of data points, and combining the values to provide the measure.

12. The computer implemented method according to claim 11, wherein the stroke features include one or more of:
   (i) pressure applied in the stroke,
   (ii) stroke velocity,
   (iii) length of the stroke,
   (iv) an altitude measure representing a tilt of a pen, stylus, finger or other pointing device used to produce the hand-based strokes,
   (v) an azimuth measure representing a rotation of a pen, stylus, finger or other pointing device used to produce the hand-based strokes,
   (vi) the stroke features (ii) to (v) for movement between strokes.

13. The computer-implemented method according to claim 1, wherein the method is displayed on a computer generated display or stored in computer non-volatile memory.

14. A computer system that changes its output based on determination of a person's cognitive load while performing a task comprising:
   an interactive interface to sense stroke data comprising data points, each having a time reference and a spatial reference, wherein the stroke data is representative of hand-based strokes produced by a person while performing a task on the computer system via the interactive interface; and
   a processor to perform the following:
   receive the stroke data sensed by the interactive interface;
   identify sets of data points in the stroke data that have adjacent spatial references for each time reference in time series order, each of the sets of data points representing a hand-based stroke;
   determine that one or more of the sets of the data points in the stroke data meets one or more predetermined stability criteria by having a variance that is less than a threshold and select the one or more of the sets of data points;
   identify one or more predetermined stroke features in the selected one or more of the sets of data points and determine a measure indicative of the person's cognitive load based on the one or more predetermined stroke features identified in the selected one or more of the sets of data points; and
   automatically change an output of the computer system based on the measure indicative of the person's cognitive load to alleviate or increase the person's cognitive load.

15. A non-transitory computer-readable media, including instructions, when executed by a computer, causes the computer to:
   (a) receive, at a processor of the computer from an interactive interface of the computer, stroke data sensed by the interactive interface, the stroke data comprising data points each having a time reference and a spatial reference, wherein the stroke data is representative of hand-based strokes produced by a person while performing a task on the computer via the interactive interface;
   (b) identify, by the processor, sets of data points in the stroke data that have adjacent spatial references for each time reference in time series order, each of the sets of data points representing an individual hand-based stroke;
   (c) determine by the processor, that one or more of the sets of data points in the stroke data meets one or more predetermined stability criteria by having a variance that is less than a threshold and selecting, by the processor, the one or more of the sets of data points;
   (d) identify, by the processor, one or more predetermined stroke features in the selected one or more of the sets of data points, and determine, by the processor of the computer, a measure indicative of the person's cognitive load based on the one or more predetermined stroke features identified in the selected one or more of the sets of data points; and
   (e) automatically change an output of the computer, via the processor, based on the measure indicative of the person's cognitive load to alleviate or increase the person's cognitive load.

16. The computer-implemented method according to claim 1, wherein automatically change an output of the computer system, via the processor, based on the measure indicative of the person's cognitive load comprises one or more of the following:
   providing adaptive hints according to the current cognitive load;
   modulating one or more of the pace, content, and format of the output in real-time; and
   adjusting the difficulty of the task according to the detected cognitive load.

* * * * *